US006592845B2

(12) United States Patent
Uckun et al.

(10) Patent No.: US 6,592,845 B2
(45) Date of Patent: *Jul. 15, 2003

(54) ESTROGENS FOR TREATING ALS

(75) Inventors: Fatih M. Uckun, White Bear Lake, MN (US); Vuoung N. Trieu, Roseville, MN (US); Xing-Ping Liu, Minneapolis, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/007,967

(22) Filed: Nov. 2, 2001

(65) Prior Publication Data

US 2002/0052385 A1 May 2, 2002

Related U.S. Application Data

(63) Continuation of application No. 09/455,846, filed on Dec. 7, 1999, now Pat. No. 6,334,998.

(51) Int. Cl.[7] .............................................. A61K 49/00
(52) U.S. Cl. ..................... 424/9.1; 424/9.2; 424/1.11; 549/273
(58) Field of Search ................... 424/1.11, 9.1, 424/9.2, 489, 1.65; 549/273; 552/502; 540/21

(56) References Cited

U.S. PATENT DOCUMENTS 6,334,998 B1 * 1/2002 Uckun et al. ................. 424/9.1

FOREIGN PATENT DOCUMENTS

| EP | 0 832 886 A1 | 4/1998 |
| WO | WO 98/11923 | 3/1998 |
| WO | WO 99/61428 | 12/1999 |

OTHER PUBLICATIONS

Avis, K. E., "Parental Preparations," *Remington's Pharmaceutical Sciences*, Fifteenth Edition, Mack Publishing Company, pp. 1461–1487 (1975).

Borchelt, D. R. et al., "Transgenic Mouse Models of Alzheimer's Disease and Amyotrophic Lateral Sclerosis," Symposium: Transgenic Models of Neurodegeneration, *Brain Pathology*, vol. 8, pp. 735–757 (1998).

Brooks, B. R., "World Federation of Neurology Research Group on Neuromuscular Diseases, El Escorial, World Federation of Neurology Criteria for the Diagnosis of Amyotrophic lateral Sclerosis," *Journal of the Neurological Sciences*, vol. 124 (Suppl.), pp. 96–107 (1994).

Dal Canto, M. C. et al., "Short Communication: Development of Central Nervous System Pathology in a Murine Transgenic Model of Human Amyotrophic Lateral Sclerosis," *American Journal of Pathology*, vol. 145, No. 6, pp. 1271–1279 (Dec. 1994).

Deardorff, D. L., "Isotonic Solutions," *Remington's Pharmaceutical Sciences*, Fifteenth Edition, Mack Publishing Company, pp. 1405–1412 (1975).

Deng, H. et al., "Amyotrophic Lateral Sclerosis and Structural Defects in Cu,Zn Superoxide Dismutase," *Science*, vol. 261, pp. 1047–1051 (Aug. 20, 1993).

Hilakivi–Clarke, L. et al., "Maternal genistein exposure mimics the effects of estrogen on mammary gland development in female mouse offspring," *Oncology Reports*, vol. 5, pp. 609–616 (1998).

Hirano, A., "Neuropathology of ALS," *Neurology*, vol. 47 (Suppl. 2), pp. S63–S66 (1996).

Hughes, J. T., "Pathology of Amyotrophic Lateral Sclerosis," *Human Motor Neuron Diseases*, pp. 61–74 (1982).

Munsat, T. L., "3: The Natural History of Amyotrophic Lateral Sclerosis," *Handbook of Amyotrophic Lateral Sclerosis*, pp. 65–75 (1992).

Narasimhachari, N. et al., "Synthetic Experiments in the Benzopyrone Series: Part XXXV—Use of Methyl Formate in Isoflavone Condensation: Isolation of 2–Hydroxy Isoflavanones," *J. Sci. Industr. Res.*, vol. 12B, pp. 287–293 (1953).

Paganini–Hill, A. et al., "Postmenopausal oestrogen treatment and stroke: a prospective study," *BMJ*, vol. 297, pp. 519–522 (Aug. 1988).

Reed, D. M. et al., "Amyotrophic Lateral Sclerosis and parkinsonism–Dementia on Guam, 1945–1972, I. Descriptive Epidemiology," *American Journal of Epidemiology*, vol. 101, No. 4, pp. 287–301 (1975).

Rosen, D. R. et al., "Mutations in Cu/Zn superoxide dismutase gene are associated with familial amyotrophic lateral sclerosis," *Nature*, vol. 362, pp. 59–62 (Mar. 4, 1993).

Rudnicki, "Estrogen Replacement Therapy in Women with Amyotrophic Lateral Sclerosis", *Journal of the Neurological Sciences*, vol. 169, Nos. 1–2, pp. 126–127 (Oct. 31, 1999).

Ruiz–Larrea, M. B. et al., "Antioxidant Activity of Phytoestrogenic Isoflavones," *Free Rad. Res.* vol. 26, pp. 63–70 (1997).

Santell, R. C. et al., "Dietary Genistein Exerts Estrogenic Effects upon the Uterus, Mammary Gland and the Hypothalamic/Pituitary Axis in Rats," *Biochemical and Molecular Roles of Nutrients*, pp. 263–269 (1997).

(List continued on next page.)

Primary Examiner—Dameron L. Jones
(74) Attorney, Agent, or Firm—Merchant & Gould P.C.

(57) ABSTRACT

A method for preventing and treating ALS by administering a phytoestrogen, preferably genistein.

2 Claims, 3 Drawing Sheets

OTHER PUBLICATIONS

Siddique, T. et al., "Linkage of a Gene Causing Familial Amyotrophic Lateral Sclerosis to Chromosome 21 and Evidence of Genetic–Locus Heterogeneity," *The New England Journal of Medicine*, vol. 324, No. 20, pp. 1381–1384 (May 16, 1991).

Stampfer, M. J. et al., "Postmenopausal Estrogen Therapy and Cardiovascular Disease," *The New England Journal of Medicine*, vol. 325, No. 11, pp. 756–762 (Sep. 12, 1991).

Trieu et al., "Genistein is Neuroprotective in Murine Models in Familial Amyotrophic Lateral Sclerosis and Stroke", *Biochemical and Biophysical Research Communications*, vol. 258, No. 3, pp. 685–688 (May 19, 1999).

Wähälä, K. et al., "Expedient Synthesis of Polyhydroxyisoflavones," *J. Chem. Soc. Perkin Trans.*, pp. 3005–3008 (1991).

Yoshida, S. et al., "Follow–Up Study on Amyotrophic Lateral Sclerosis in Rochester, Minn., 1925 through 1984," *Neuropidemiology*, vol. 5, pp. 61–70 (1986).

Zava, D. T. et al., "Estrogenic Activity of Natural and Synthetic Estrogens in Human Breast Cancer Cells in Culture," *Environmental Health Perspectives*, vol. 105, Supplement 3, pp. 637–645 (Apr. 1997).

Trieu, V. et al., "Genistein is Neuroprotective in Murine Models of Familial Amyotrophic Lateral Sclerosis and Stroke", Biochemical and Biophysical Research Communications vol. 258, No. 3, pp 685–688 (1999).

Trieu, V. et al., "Neuroprotective Activity of A Phytoestrogen, Genistein, Against Photochemically Induced Thrombotic Stroke and Familial Amyotrophic Lateral Sclerosis", XP—002197490, p. 845 (Aug. 1999).

\* cited by examiner

ESTROGENS FOR TREATING ALS

RELATED APPLICATION

This application is a § 1.53(b) continuation of U.S. Ser. No. 09/455,846, filed Dec. 7, 1999, now U.S. Pat. No. 6,334,998 which application is expressly incorporated by reference herein.

TECHNICAL FIELD

The invention relates to the treatment and prevention of amyotrophic lateral sclerosis (ALS) by the administration of estrogen. Pretreatment with an estrogen compound, for example, with the estrogenic isoflavone, genistein, prevents pathologic conditions associated with ALS and delays disease onset in individuals at high risk for ALS.

BACKGROUND

Amyotrophic lateral sclerosis (ALS), also known as Lou Gehrig's disease, is a progressive, fatal neurodegenerative disorder involving the motor neurons of the cortex, brain stem, and spinal cord (Hirano, A., 1996, Neurology 47 (Suppl. 2), S63–S66). It is a degenerative disease of upper and lower motor neurons that produces progressive weakness of voluntary muscles, with eventual death. The onset of disease is usually in the fourth or fifth decade of life, and affected individuals succumb within 2 to 5 years of disease onset. ALS occurs in both sporadic and familial forms. About 10% of all ALS patients are familial cases, of which 20% have mutations in the superoxide dismutase 1 (SOD1) gene (formerly known as Cu,Zn-SOD), suggesting that an abnormally functioning Cu,Zn-SOD enzyme may play a pivotal role in the pathogenesis and progression of familial amyotrophic lateral sclerosis (FALS) (Rosen et al., 1993, Nature 362: 59; Siddique et al., 1991, N. Engl. J. Med. 324:1381).

More than 50 point mutations of the human SOD1 gene have been found in patients with FALS. Most of the mutations occur at regions involved in the subunit folding exposing the active site to the outside, leading to increased hydroxyl radical generation. It is believed that the increased generation of oxygen free radicals, especially hydroxyl radicals, by mutant SOD1, to be the initiating factor that results in the sequence of events leading to motor neuron death in FALS. This hypothesis is supported by recent reports that transfection of neuronal precursor cells with mutant SOD1 results in increased production of hydroxyl radicals and enhanced rate of cell death by apoptosis (Liu et al., 1999, Radiat. Res. 151:133).

The incidence of ALS in males is higher than in females (Reed and Brody, 1975, Am. J. Epidemiol. 101:287; Yoshida et al., 1986, Neuroepidemiology 5:61), indicating a sexual dimorphic etiology. It is known that estrogen therapy can produce beneficial effects for a variety of diseases, however, estrogen has not previously been suggested as useful in the treatment of ALS.

Estrogen treatment reportedly lowers the incidence of cardiovascular diseases and stroke mortality 70% and 36%, respectively (Stampfer et al., 1991, N. Engl. J. Med., 325: 756–762; Paganini-Hill et al., 1988, Br Med J, 297: 519–522). Physiological events, such as improved cerebrovascular blood flow, as well as cellular events, such as attenuation of neuronal cell death from glutamate toxicity and oxidative stress, are all involved in the neuroprotective activity of estrogen.

Phytoestrogens are non-steroidal plant compounds that have estrogenic activity in humans and animals. Genistein is a phytoestrogen exhibiting weak estrogen activity both in vitro and in vivo (Santel et al, 1997, J. Nutr, 127:263–269; Hilakivi-Clarke et al., 1998, Oncol Rep, 5: 609–616; Zava et al., 1997, Environ Health Perspect, 105(Suppl. 3): 637–645). In vitro, genistein binds to the estrogen receptor and induces estrogen-regulated end products (Zava et al., 1997, supra). However, genistein, has also been shown to exhibit pleiotropic biologic activities including antioxidant activity (Ruiz-Larrea et.al., 1997 Free Rad. Res. 26:63); inhibition of tyrosine kinase activity (Uckun et.al., 1995, Science 267:886) and protective activity against radiation induced apoptotic cell death (Uckun et.al., 1992, PNAS USA 89:9005).

Despite having been studied for over 100 years, the etiology of ALS is still largely unknown with no clearly effective treatment or method of prevention. Methods and compositions that prevent or ameliorate the neurologic damage indicative of ALS are needed. Accordingly, there is a need for a method or composition that prevents or delays onset of pathologic conditions related to ALS. In the present invention, phytoestrogens such as the isoflavone genistein, are demonstrated to be effective as a neuroprotective compounds which can delay onset of ALS and pathological symptoms associated with this disease.

SUMMARY

The present invention provides methods for preventing and/or delaying symptoms, or treating symptoms relating to amyotrophic lateral sclerosis (ALS). More particularly, the invention provides estrogens, particularly phytoestrogens, and preferably estrogenic flavonoid compounds having one or more hydroxylated aromatic rings, for the treatment of ALS. Preferred estrogens include genistein and effective analogs of genistein, coumestrol, zeanoloval, 4-(4'-hydroxylphenyl)-amino-6,7-dimethoxyquinazoline (P131) and 2,4,4'-trihydroxy deoxybenzoin (DDE-17) for administration to a subject for the prevention and/or treatment of ALS Preferably, the estrogen is administered to a patient before the onset of ALS. Administration of the estrogen to the patient, can be, for example, systemically, or locally into a tissue.

A patient to be treated by the method of the invention is one determined to be susceptible to ALS, one exhibiting a symptom associated with ALS, or one diagnosed as suffering from ALS. Patients susceptible to ALS include patients at risk of developing ALS. These would include, for example, patients with a family history or predisposition to developing ALS, and the like. Indications that a patient is susceptible to ALS include those individuals testing positive for molecular markers indicative of or associated with ALS. Such markers include, for example, any one of the known mutations in the SOD1 gene (Deng et al., 1993, Science, 261: 1047–1051).

Accordingly, one embodiment of the present invention includes a method for preventing onset of ALS, including the step of administering to a subject, prior to the onset of ALS, an effective amount of an estrogen, such as coumestrol, zearolonal, or genistein. Preferred is the administration of a hydroxy-substituted estrogenic isoflavone having the general formula I shown below. The invention also includes prevention of disease progression by administering such a compound; and also use of estrogens for the treatment of ALS disease symptoms.

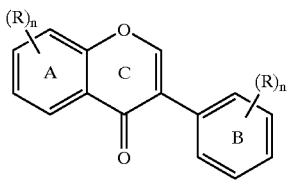

R is $NH_2$, halo, $C_1$–$C_6$ alkyl, or OR' and n is 1 to 4, wherein at least one R is OR', and R' is H, $C_1$–$C_6$ alkyl, or a sugar moiety. (It is common for a sugar moiety to bind the flavone via reaction with the flavone's hydroxyl groups.) One or both of the rings, A and B, each comprise one or more hydroxyl groups (R). Preferred are phytoestrogens and their active estrogenic derivatives. Most preferred is the estrogenic isoflavone, genistein, shown below.

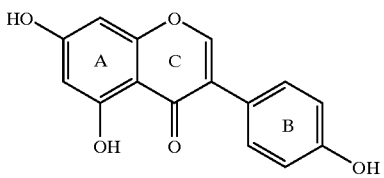

The above summary of the present invention is not intended to describe each disclosed embodiment or every implementation of the present invention. The Figures and the detailed description which follow more particularly exemplify these embodiments.

DETAILED DESCRIPTION

Figure 1:
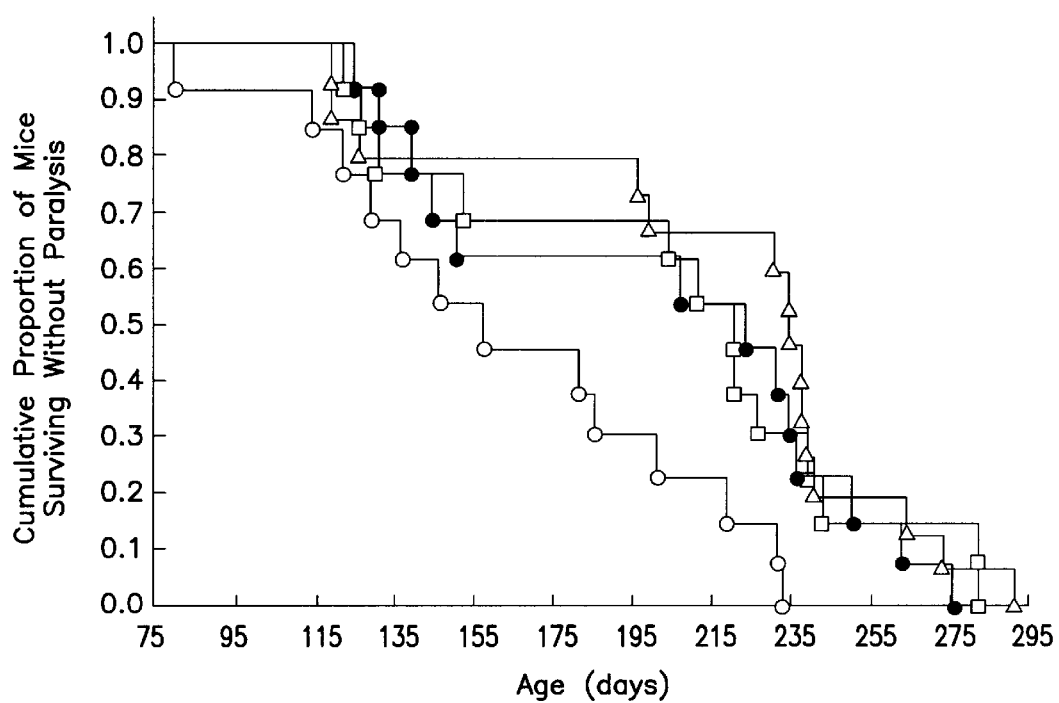
FIG. 1 is a graph showing delayed disease onset and mortality in male FALS mice treated with genistein.

The invention provides methods for preventing, treating and/or ameliorating the effects of neurological injury induced in tissues due to ALS.

While the invention is amenable to various modifications and alternative forms, specifics of the invention are shown by example and will be described in detail. It should be understood, however, that the intention is not to limit the invention to the particular embodiments described. On the contrary, the intention is to cover all modifications, equivalents, and alternatives falling within the spirit and scope of the invention.

Definitions

All scientific and technical terms used in this application have meanings commonly used in the art unless otherwise specified. As used in this application, the following words or phrases have the meanings specified.

As used herein, "therapeutically effective amount" is meant to define a dose or predetermined amount of the drug that provides protection against damage due to ALS, or that reduces, alleviates, prevents the onset of, or prevents the progression of one or more symptoms associated with ALS. A amount of phytoestrogen expected to be therapeutically effective is a daily dose in the range of about 10 to 100 mg/kg body weight.

As used herein, "alkyl", which includes the alkyl group of "alkoxy" substituents, is meant to define both branched and straight-chain saturated aliphatic hydrocarbon groups having the specified number of carbon atoms, for example $C_1$–$C_6$. As a preferred embodiment, "alkyl" means chains of 1 to 4 carbon atoms, for example, methyl, ethyl, propyl, isopropyl, butyl, secondary butyl, t-butyl, and the like.

As used herein, "halogen" or "halo" substituent means fluoro, chloro, bromo, and iodo.

As used herein, "treating" means the prevention or reduction of severity of symptoms or effect of a pathological condition, including prolonging life expectancy. In the context of ALS therapy, treatment includes "prevention" or inhibition of the onset of disease symptoms associated with or indicative of ALS, such as limb paralysis, muscle weakness, and/or neurodegeneration of the motor cortex.

As used herein, "at risk" means an individual who has a familial or genetic predisposition indicative of ALS; an individual who carries a marker found to be associated with or correlative to ALS.

Compounds of the Invention

Compounds useful in the method of the invention are estrogens, as described above. The estrogenic activity of a compound may be determined by known methods, for example by assay of estrogen receptor binding activity or by bioassay of estrogenic function.

Preferred phytoestrogen compounds of the invention include genistein, coumestrol, zearolonal, Luteolin, diadzin, aminogenistein, quercetin, and the like. Most preferred are estrogenic isoflavones such as genistein and 2,4,4'-trihydroxy deoxybenzoin (DDE-17).

The general structure of the preferred estrogens is shown below, where R is $NH_2$, halo, $C_1$–$C_6$ alkyl, or OR' and n is preferably 1 to 4, where at least one R is OR', and R' is H, $C_1$–$C_6$ alkyl, or a sugar moiety.

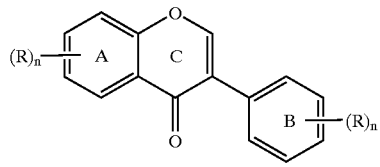

A most preferred isoflavone is genistein, having the structure shown below:

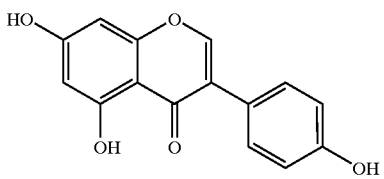

Active analogs may also be used. For example, for purposes of this invention, an active analog of genistein is defined as a compound structurally related to genistein, for example a different flavonoid, which is effective in reducing the size of induced ischemic lesions in tissue, for example, as analyzed in the non-invasive murine mouse model described in the Examples below. Such active analogs of genistein include, for example, amino-genistein and other such derivatives of genistein which retain estrogenic activity and the ability to ameliorate symptoms of ALS or prevent onset of ALS. It is understood that the estrogenic compounds of the invention may be modified in numerous ways without affecting the estrogenic activity useful in the invention. Such modifications, analogs, and derivatives are within the scope of "estrogens" of the invention.

The naturally occurring isoflavone, genistein, is demonstrated herein to have protective effects against symptoms of ALS and is useful as a prophylactic agent for prevention and treatment of ALS. While not meant to limit the invention, it is believed that this protective effect is due to the estrogenic activity of the administered phytoestrogen.

Genistein is a phytoestrogen found in soy products (Narasimhachari et al., 1953, *J. Sci. Ind. Res.* 12:287). Genistein may be synthesized as described by Wahala et al., 1991, *Journal of the Chemical Society of Perk Trans* 1:3005, and as described in the synthetic scheme shown below.

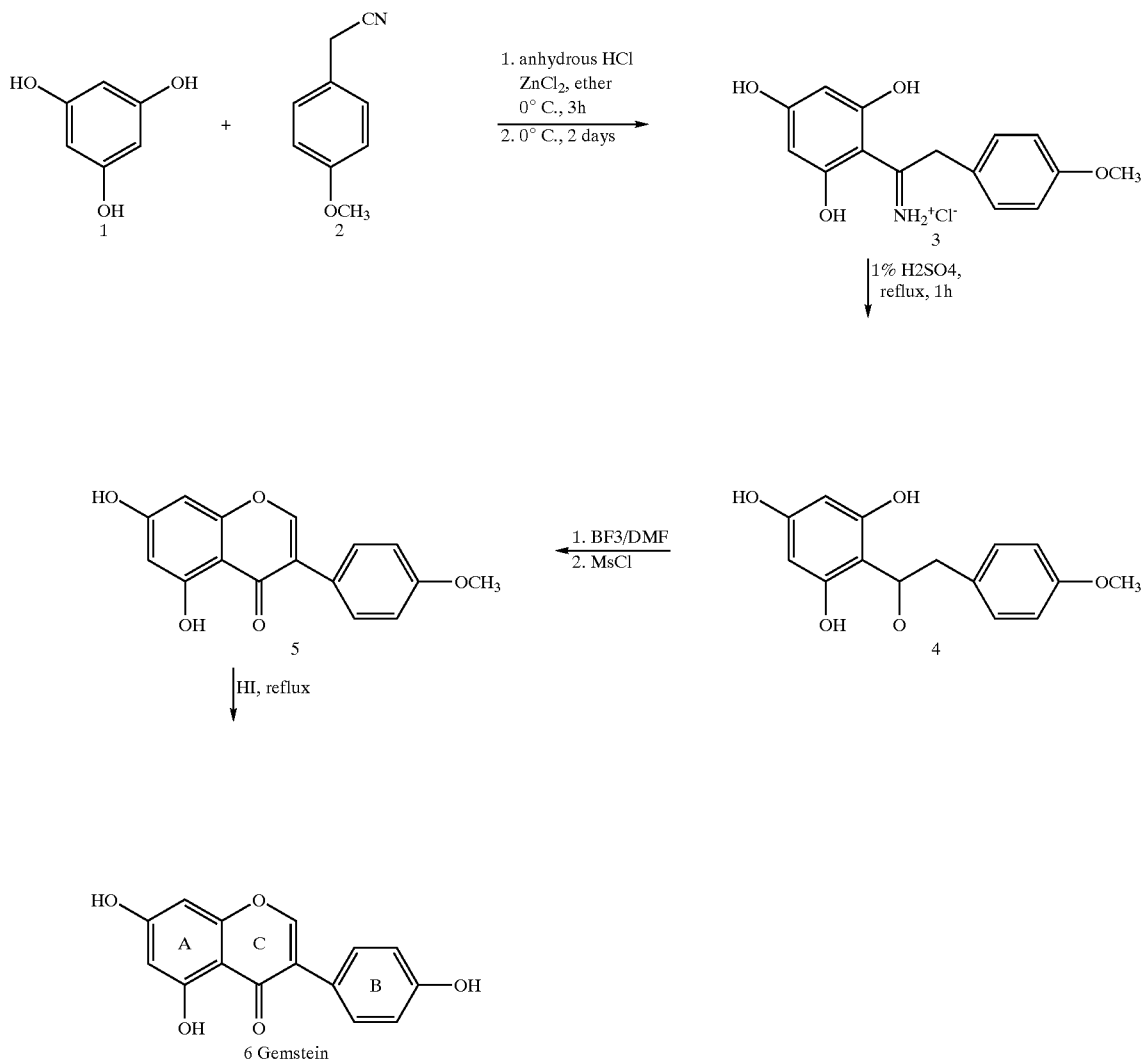

Preferred compounds of the invention are genistein and active analogs thereof. Other estrogens can also be used in the method of the invention. These include, for example, coumesterol, zearalonol, and 2,4,4'-trihydroxy deoxybenzoin (DDE-17).

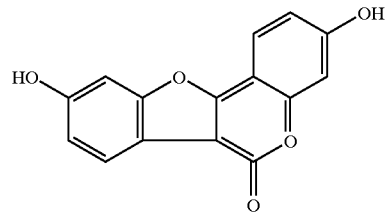

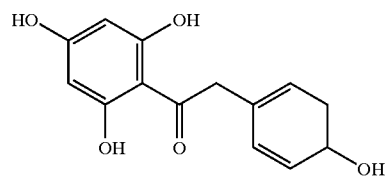

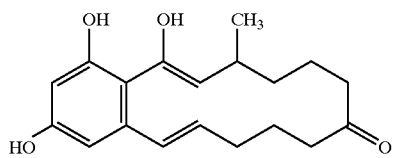

Coumesterol          DDE-17          Zearalonol

Methods and Pharmaceutical Compositions

In the method of the invention, estrogens are prepared in pharmaceutical compositions for treatment and prevention of conditions that give rise to ALS and to neuronal tissue damage due to ALS. Patient treatment using the method of the present invention involves administering therapeutic amounts of an estrogen composition.

In the context of the present invention, the terms "treat", "therapy", and the like are meant to include methods to alleviate, slow the progression, prevent, attenuate, or cure the treated disease.

The pharmaceutical compositions of the present invention include an estrogen in effective unit dosage form and a pharmaceutically acceptable carrier. As used herein, the term "effective amount", "effective unit dosage" or "effective unit dose" is meant to define a predetermined amount of the drug that provides protection of cells or tissues against damage due to onset or progression of ALS, or lessons a symptom indicative of ALS such as limbic paralysis, muscle wasting, weakness or cramping. An amount of isoflavone expected to be effective is a daily dose in the range of about 10 to 100 mg/kg.

Pharmaceutically acceptable carriers are materials useful for the purpose of administering the medicament, which are preferably non-toxic, and can be solid, liquid, or gaseous materials, which are otherwise inert and medically acceptable and are compatible with the active ingredients. Suitable pharmaceutical carriers and their formulations are described in Martin, "Remington's Pharmaceutical Sciences," 15th Ed.; Mack Publishing Co., Easton (1975); see, e.g., pp. 1405–1412 and pp. 1461–1487. Such compositions will, in general, contain an effective amount of the active compound together with a suitable amount of carrier so as to prepare the proper dosage form for proper administration to the host.

The pharmaceutical composition may also be combined with or conjugated to specific delivery agents, including targeting antibodies and/or cytokines. The pharmaceutical composition can include pharmaceutically acceptable salts of the active estrogen. Pharmaceutically acceptable salts include salts of any potentially charged group in the compound, such as a salt of any amine. Suitable salts include gluconate salts, chloride salts, and the like. Such conjugated estrogens, salts, prodrugs, and the like are considered within the scope of "estrogens" of the invention.

Conjugation to a Targeting Moiety

The composition of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compounds which serves to deliver the compound of the invention to a specific site for the desired activity. Targeting moieties include, for example, molecules which specifically bind molecules present on a cell surface. Such targeting moieties useful in the invention include anti-cell surface antigen antibodies. Particularly useful targeting moieties for targeting the compounds of the invention to cells for therapeutic activity include those ligands that bind known antigens or receptors present on the neurons to be treated.

Administration Methods

A composition of the invention may be formulated with conventional pharmaceutically acceptable parental vehicles for administration by injection. These vehicles comprise substances which are essentially nontoxic and nontherapeutic such as water, saline, Ringer's solution, dextrose solution, Hank's solution, a perfusion solution, and the like. It is to be understood that isoflavone formulations may also include small amounts of adjuvants such as buffers and preservatives to maintain isotonicity, physiological and pH stability. The compositions according to the invention can be presented in unit dose form in ampules or in multi-dose containers with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile, pyrogen-free buffer saline, before use. The present compositions can also be in the form of encapsulated liposomes or other sustained release formulations.

As indicated by the above formulation, the composition can be administered parenterally. The composition can be administered by known techniques such as orally, for example, in tablets, capsules, enterically coated capsules and the like, or in drops, among other methods such as by inhalation spray, topically, by transdermal patches or by absorption through a mucous membrane, or rectally, in dosage unit formulations containing conventional non-toxic pharmaceutically acceptable carriers, adjuvants or vehicles. When administered intravenously, it can be delivered as a bolus or on a continuous basis. The composition can be administered intrarterially such as through a catheter. A preferred method of administration is intravenous administration of a sustained release formulation.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For rectal administration as suppositories, the compositions can be prepared by mixing with a suitable non-irritating excipient, such as cocoa butter, synthetic glyceride esters or polyethylene glycols, which are solid at ambient temperatures, but liquify or dissolve in the rectal cavity to release the drug.

The dose of the estrogen formulation to be administered will depend upon the patient and the patient's medical history, and the severity of the disease process. However, the dose should be sufficient to effectively precondition against ALS, or to effectively prevent, reduce, or inhibit damage due to ALS. Dosages for adult humans envisioned by the present invention and considered to be therapeutically effective will preferably range from between about 10 mg/kg and about 100 mg/kg. These doses may be repeated up to several times per day. In addition, lower and higher doses may be more appropriate depending on the individual patient and the degree of condition to be treated.

Typically, the compositions of the invention will be administered to a patient (human or other animal, including mammals) in need thereof, in an effective amount to reduce or prevent damage from ALS. The present compositions can be given either orally, intravenously, intramuscularly or topically.

The composition can be administered to a patient or locally to a tissue. When administered to a patient, the composition can be administered systemically, or directly to an organ or tissue, for example through a catheter to the blood stream entering the tissue or organ, or via the spinal column for access to cerebral fluids of the brain. Alternatively, the composition can be administered via injection directly into the tissue or organ, or into other fluids or solutions that enter the organ, such as lymph or iv solutions.

The composition is preferably administered before damage due to ALS occurs. For example, if it is known that a patient is at high risk of ALS because of diagnostic indicators, or a family history of ALS, prophylactic treatment with an isoflavone in accord with the invention is indicated. Preferably, the estrogen is administered prior to patient presentation of symptoms indicative of ALS.

Clinical Features of ALS

ALS generally presents with a characteristic pattern of lesions involving motor neurons of the brain stem and anterior horn area of the spinal cord. There is also involvement of the large pyramidal neurons of the motor cortex, with pathological changes found in the extramotor cortex, in the cerebrospinal and sensory systems as well as in the subcortical regions (Hughes, J. T., 1982, Pathology of amyotrophic lateral sclerosis. In: Rowland LP (ed) Human motor neuron disease. (Advances in Neurology, vol 36). The criteria for diagnosis of ALS has been established by the World Federation of Neurology (Brooks, B. R., 1994, El Escorial World Federation of Neurology criteria for the diagnosis of amyotyrophic lateral sclerosis. Subcomittee on Motor Neurone Diseases/Amyotrophic Lateral Sclerosis of the World Federation of Neurology Research Group on Neuromuscular Diseases and the El Escorial 'Clinical limits of amyotrophic lateral sclerosis' workshop contributors. *J. Neurol Sci* [Suppl] 124:96–107). An overview of the neuropathologic findings in patients with ALS is presented by A. Hirano (1996, Neuropathology of ALS: an overview, *Neurology*, 47 (Suppl 2): S63–S66).

ALS is characterized by paralysis, muscular atrophy, spasticity, and a variety of other motor signs. The natural history of ALS is well documented (Munset T. L., 1992, The natural history of amyotrophic lateral sclerosis. In: *Handbook of Amyotrophic Lateral Sclerosis,* Smith R A (eds.), Chapter 2, pp. 39–63, Marcel Dekker, Inc.: New York). The presenting symptoms of ALS include, for example, muscle wasting or weakness of the hands or legs. Occasionally, cramps and fasciculations precede the common presenting symptoms. Bulbar symptoms consisting of dysarthria or dysphagia appear as the disease progresses, but can also be the presenting complaints in some of the patients. Such patients may be placed on a prophylactic regimen as long as risk remains high as determined by standard diagnostic indicators. The preferred method is to administer an effective amount of a phytoestrogenic compound, such as an isoflavone to a patient at high risk for ALS.

A patient or tissue may also be treated by the method of the invention after some damage due to ALS has occurred to minimize further damage from additional neuropathological events. An isoflavone according to a method of the invention can be administered for example after a transient episode. An effective amount is that amount which reduces symptoms such as lymbic paralysis.

In general, a dose which delivers about 10 to 100 mg/kg body weight administered for at least about 24 hours after presentation or diagnosis is expected to be effective, although more or less may be useful. One skilled in the art will use standard procedures and patient analysis to calculate the appropriate dose, extrapolating from the data provided in the Examples. In addition, the compositions of the invention may be administered in combination with other therapies for ALS. In such combination therapy, the administered dose of the isoflavone may be less than for single drug therapy.

A patient presenting with symptoms indicative of ALS may also be treated by the method of the invention to prevent progression of the disease or to prevent the development of more severe symptoms. A patient with ALS may also be treated by the method of the invention to lessen the symptoms of ALS and/or to extend the patient's longevity. As disclosed below, genistein inhibits disease onset and delays death in an animal model of ALS, thus providing an effective method for the treatment and prevention of ALS.

One or more of the following clinical evaluations can be used to assess progress/prevention of ALS disease.

(1) Quantitative Strength and Functional markers: The TUFTS Quantitative Neuromuscular Examination (TQNE) is a well standardized, reliable, validated test to measure strength and function in ALS. The test involves measurement of maximum voluntary isometric contraction (MVIC) of 8 muscle groups in the arms using a strain gauge tensiometer. This measurement is a standard for clinical trials in ALS.

(2) Functional measures: The ALS Functional Rating Scale (ALSFRS) is an easily administered ordinal rating scale used to determine patients' assessment of their ability and independence in 10 functional activities. Validity has been established by correlating ALSFRS scores with change in strength over time. The ALSFRS is generally a secondary outcome measure in clinical trials.

(3) Measures of Upper Motor Neuron Function by traditional methods.

EXAMPLES

The present invention may be better understood with reference to the following examples. These examples are intended to be representative of specific embodiments of the invention, and are not intended as limiting the scope of the invention.

Example 1

Sexual Dimorphism in a Murine Model of FALS

Heterozygous transgenic mice carrying the human SOD-1 (G93A) were obtained from Jackson Laboratory (Bar Harbor, Me., USA). These mice were monitored everyday for limbic paralysis and death. Onset of FALS was defined as the first day upon which limbic paralysis was observed. Life-table analysis was performed using Statview, Abacus Concepts, Inc. (Berkeley, Calif.).

There are currently several transgenic animal models of ALS (Borchelt et al., 1998, Transgenic mouse models of Alzheimer's disease and amyotrophic lateral sclerosis, *Brain Pathology*, 8: 735–757). The G93A HuSOD1 is a well established animal model of familial ALS which has been described previously in detail (Dal Canto M C, Gurney Me., 1994, The development of central nervous system pathology in a murine transgenic model of human amyotrophic lateral sclerosis. *Am J. Pathol* 145: 1–9; Gurney et al., 1994, Motor neuron degeneration in mice that express a human Cu,Zn superoxide dismutase mutation, *Science* 264:1772–1775). Levels of SOD1 activity are elevated to about five times above that of endogenous SOD 1 in these mice. In this model, the mice develop hind limb weakness, a coarse coat, poor grooming, and reduced stride length at about 3 months of age. By five months of age, a majority of the mice are moribund.

Among individuals diagnosed with ALS, there is a high male to female ratio of incidence (Reed, D. M., Brody J. A., 1975, *Am J. Epidemiol.* 101:287–301; Yoshida et al., 1986, *Neuroepidemiology* 5:61–70). The above-described G93A HuSOD1 mice were employed to examine the sexual dimorphism of ALS in an animal model of this disease.

As shown in FIG. 1, male FALS mice (open circles) exhibited an earlier disease onset and death as compared to female FALS mice (triangles). Female FALS mice exhibited significantly delayed disease onset and mortality when compared to male FALS mice (p=0.001 and p=0.01, respectively, log-rank statistic). These results indicate that the female sex hormone, estrogen, may be protective against FALS.

Example 2

Genistein is Neuroprotective Against ALS

The ability of the isoflavone genistein to protect against neural degeneration in a murine model of familial ALS was evaluated. Genistein was synthesized as reported previously (Uckun et al., 1995, *Science*, 267: 886–891).

Heterozygous transgenic mice carrying the human SOD-1 (G93A) were obtained from Jackson Laboratory (Bar Harbor, Me., USA). The mice were treated either with vehicle or genistein at 16 mg/kg twice a day, everyday, except on weekends. The mice were monitored everyday for limb paralysis and death. Onset of FALS was defined as the first day upon which limbic paralysis was observed. Life-table analysis was performed using Statview, Abacus Concepts, Inc. (Berkeley, Calif.).

FALS mice were divided into the 4 groups: (males treated with vehicle (open circles, n=13) or genistein (filled circles, n=13); and females treated with vehicle (triangles, n=15)or genistein (squares, n=13)). Genistein treatment delayed the disease onset and mortality in male FALS mice (p=0.02 and p=0.02, respectively, long-rank statistic), with curves superimposible on those of female FALS mice (see FIG. 1), indicating that the phytoestrogen, genistein, is neuroprotective in FALS mice.

Phytoestrogen treated females (squares) did not exhibit a delay in disease onset in comparison to untreated females (triangles), suggesting that phytoestrogens and endogenous estrogen operate through common pathway(s). Taken together, these results provide unprecedented evidence that phytoestrogens, and particularly genistein, are useful as a prophylactic agents for prevention of neurodegenerative symptoms in individuals who are at high risk for ALS as well as providing effective treatment against ALS.

Example 3

Compounds for Neuroprotection Against ALS

The ability of 4-(4'-hydroxylphenyl)-amino-6,7-dimethoxyquinazoline (P131) and 2,4,4'-trihydroxy deoxybenzoin (DDE-17) to protect against neural degeneration in familial ALS was evaluated using the methods described above for Example 2. P131 and DDE17 have the structures shown below:

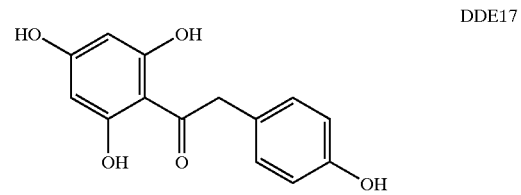

-continued

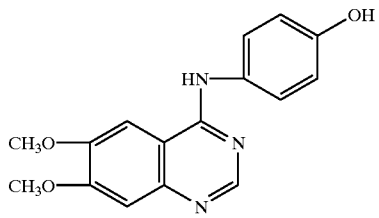

P131

DDE-17 was synthesized and characterized as described below in Example 4. The synthesis and characterization of P131 was previously described in published PCT application no. PCT/US99/11767.

Figure 2:
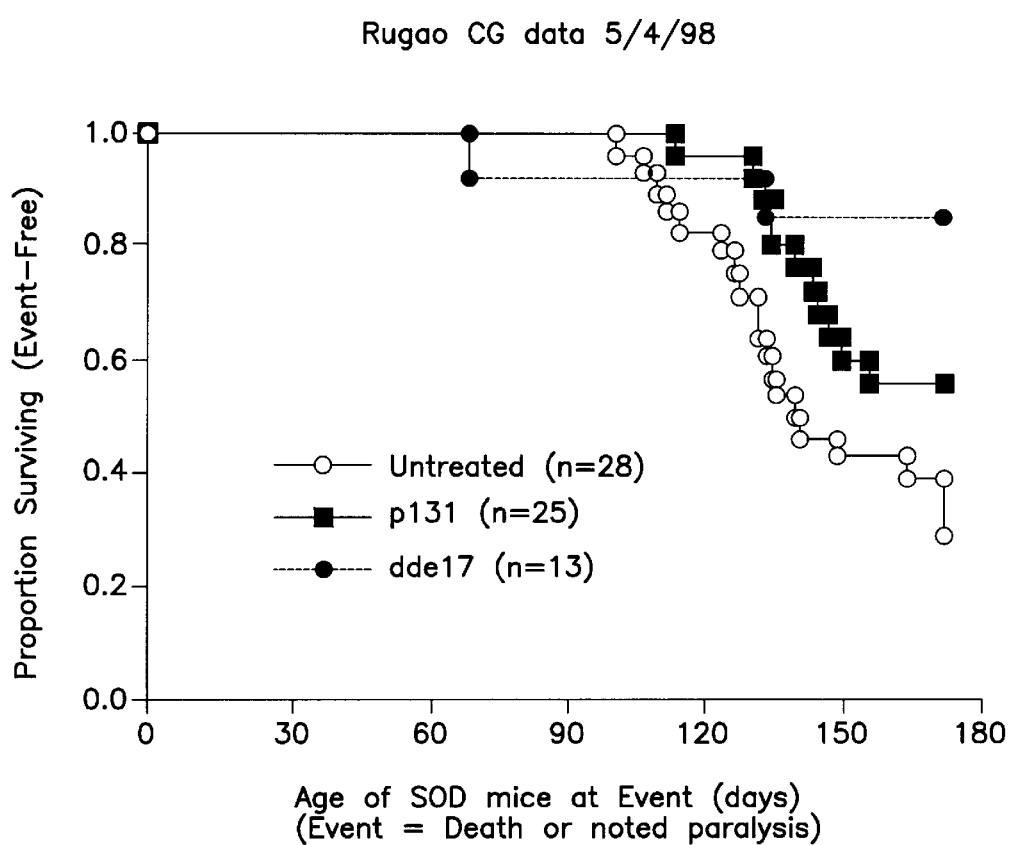
FIG. 2 is a graph showing delayed onset and mortality in male mice treated with the estrogens P131 and DDE-17.

As shown in FIG. 2, male mice treated with P131 (n=25, filled squares) and particularly those treated with DDE-17 (filled circles, n=13) demonstrated delayed onset and mortality as compared with the vehicle-treated control (open circles, n=28).

Example 4

Synthesis and Characterization of DDE-17

2, 4, 4'-trihydroxy deoxybenzoin (DDE-17) was produced according to the following scheme:

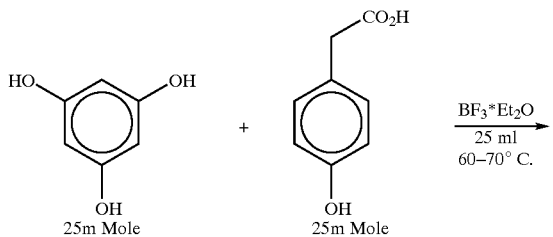

-continued

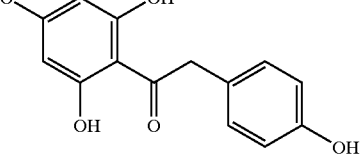

Trihydroxy benzine (25m Mole) and 4-hydroxy phenyl acetic acid (25m Mole) was transferred to a flask dried under nitrogen atmosphere. $BF_3$ $Et_2O$ (25 ml) was added and the mixture allowed to reflux on a steam bath at 70–80° C. Dry DMF was added under $N_2$ atmosphere.

Figure 3:
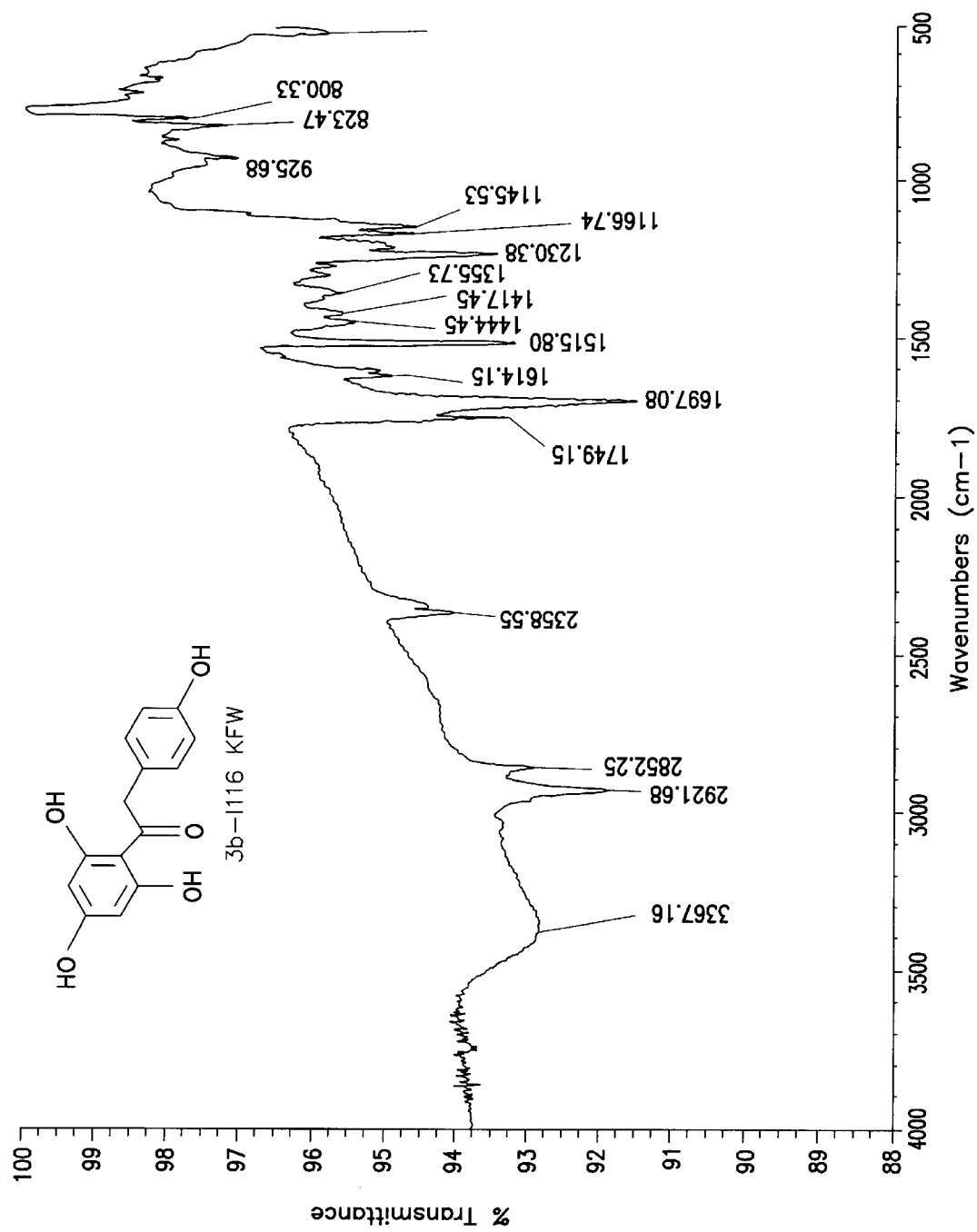
FIG. 3 is an infrared (IR) spectrum of the compound DDE-17.

An aliquot was poured into ice water acidified with HCl, extracted with $CH_2Cl_2$, and dried over $NaSO_4$. Solvent was removed under vacuum and IR taken, dissolved in CHCl. The reulting IR data is shown in FIG. 3: IR 4745, 3960, 2923, 1708, 1631, 1596 cm.

The invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A method for treating or delaying the onset of ALS, comprising:
    administering 4-(4'-hydroxyphenyl) amino-6,7-dimethoxyquinazoline to a patient suffering from or at risk of developing ALS in order to reduce symptoms or delay onset of ALS.

2. A method for ameliorating neuronal tissue damage in an ALS patient comprising administering an effective amount of 4-(4'-hydroxylphenyl)-amino-6,7-dimethoxyquinazoline to a patient diagnosed as having ALS.

* * * * *